(12) United States Patent
Jones et al.

(10) Patent No.: US 7,998,136 B2
(45) Date of Patent: *Aug. 16, 2011

(54) MEDICAL RADIATION DEVICE WITH A TAPERED FUSED WAVEGUIDE

(75) Inventors: Jeffrey W. Jones, Ropertson, WY (US); Dmitri Boutsoussov, Dana Point, CA (US)

(73) Assignee: Biolase Technology, Inc., Irvine, CA (US)

(*) Notice: Subject to any disclaimer, the term of this patent is extended or adjusted under 35 U.S.C. 154(b) by 241 days.

This patent is subject to a terminal disclaimer.

(21) Appl. No.: 12/122,689

(22) Filed: May 17, 2008

(65) Prior Publication Data

US 2008/0287941 A1  Nov. 20, 2008

Related U.S. Application Data

(63) Continuation of application No. 10/705,744, filed on Nov. 10, 2003, now Pat. No. 7,384,419.

(51) Int. Cl.
*A61B 18/18* (2006.01)

(52) U.S. Cl. ............... 606/16; 606/18; 607/88; 600/247

(58) Field of Classification Search ............ 606/1, 4–10, 606/13–18; 607/88–91; 600/247, 248; 362/317
See application file for complete search history.

(56) References Cited

U.S. PATENT DOCUMENTS

| | | | |
|---|---|---|---|
| 4,842,390 A | 6/1989 | Sottini et al. | |
| 4,898,450 A | 2/1990 | Jannson et al. | |
| 5,119,461 A | 6/1992 | Beyer et al. | |
| 5,133,709 A | 7/1992 | Prince | |
| 5,363,458 A | 11/1994 | Pan et al. | |
| 5,451,221 A * | 9/1995 | Cho et al. | 606/3 |
| 5,651,783 A | 7/1997 | Reynard | |
| 5,707,368 A | 1/1998 | Cozean et al. | |
| 5,727,108 A | 3/1998 | Hed | |
| 6,251,103 B1 | 6/2001 | Berlin | |
| 6,383,176 B1 * | 5/2002 | Connors et al. | 606/9 |
| 6,530,921 B1 * | 3/2003 | Maki | 606/15 |
| 6,942,658 B1 * | 9/2005 | Rizoiu et al. | 606/16 |
| 7,083,610 B1 * | 8/2006 | Murray et al. | 606/9 |
| 7,270,657 B2 * | 9/2007 | Rizoiu et al. | 606/16 |
| 7,384,419 B2 * | 6/2008 | Jones et al. | 606/16 |
| 7,544,204 B2 * | 6/2009 | Krespi et al. | 607/88 |
| 2003/0199860 A1 | 10/2003 | Loeb et al. | |

FOREIGN PATENT DOCUMENTS

WO  8903202 A2  4/1989

* cited by examiner

*Primary Examiner* — Ahmed Farah
(74) *Attorney, Agent, or Firm* — Stout, Uxa, Buyan & Mullins, LLP

(57) ABSTRACT

A radiation emitting apparatus is disclosed that emits a substantially homogenous beam of radiation from an irregularly shaped output end. As described herein, a radiation emitting apparatus includes a bundled fiber guide coupled to an energy distribution tuner. The bundled fiber guide is coupled to the energy distribution tuner to receive a substantially uniform distribution of high power energy. The bundled fiber guide is configured to distribute the energy to emit a substantially uniform distribution of lower power energy toward a target surface, such as a body surface. The bundled fiber guide may include a plurality of fused optic fibers, a plurality of beam splitting mirror elements, or tapered waveguides.

13 Claims, 2 Drawing Sheets

MEDICAL RADIATION DEVICE WITH A TAPERED FUSED WAVEGUIDE

CROSS-REFERENCE TO RELATED APPLICATIONS

This application is a continuation of U.S. application Ser. No. 10/705,744, filed Nov. 10, 2003, now U.S. Pat. No. 7,384,419 the entire contents of which are incorporated herein by reference.

BACKGROUND OF THE INVENTION

1. Field of the Invention

The present invention relates generally to medical devices and, more particularly, to laser handpieces.

2. Description of Related Art

Radiation delivery systems are typically used to transport electromagnetic energy from electromagnetic energy sources to treatment sites. One common radiation delivery system can comprise a cylindrically-shaped fiber optic tip from which electromagnetic energy is emitted in a direction toward the treatment site.

In certain applications, radiation delivery systems can be engineered to generate predetermined beam shapes and spatial energy distributions. The energy distribution of a simple delivery system, comprising a fiber optic tip, can be described as having a circular illumination area, with a so-called Gaussian distribution of beam intensities being spatially distributed within the illumination area. For instance, the illumination area from a fiber optic tip can comprise a central high-intensity area or "hot spot" surrounded by peripheral areas of lower intensity.

Regarding energy distributions, some beam profiling applications can require or would be optimized with radiation delivery systems capable of generating illumination areas of relatively uniform density across parts or all of the illumination area. Moreover, it may also be desirable to generate non-circular illumination areas, or to generate electromagnetic radiation having predetermined energy distributions across a non-planar illumination area. Use of laser radiation having a relatively uniform power distribution over a particularly shaped area can be a practical task for multiple medical applications. In seeking to generate predetermined energy distributions, prior-art systems have implemented relatively complex optical schemes with multiple optical elements, which systems can be relatively large and/or inefficient. A prior-art system may comprise, for example, a relatively large length, e.g., about 100 mm to 150 mm, measured from the trunk fiber to the output end of the system and measured in a direction normal to the target. Regarding efficiency, implementation of a diffuser in front of a prior-art fiber optic end together with a mirror reflector may not eliminate the "hot spot" problem and may introduce losses of laser power, which configuration can undesirably result in an efficiency as low as about 50%.

SUMMARY OF THE INVENTION

The present invention provides optical arrangements and relatively compact medical laser instruments to deliver electromagnetic radiation to treatment sites with relatively uniform power distributions over relatively wide illumination areas. The illumination areas may comprise planar surfaces in which case uniform power densities are generated throughout a cross-sectional area of the impinging radiation where the radiation intersects the treatment site; or the illumination areas may comprise non-planar surfaces, such as arched surfaces, in which case uniform power densities are generated to be relatively evenly distributed on the non-planer treatment site. The electromagnetic energy can comprise laser radiation, and the treatment site can comprise tissue to be treated.

In accordance with one aspect of the present invention, a radiation emitting apparatus includes a bundled fiber guide coupled to receive electromagnetic radiation from an energy distributor, such as an energy-distribution tuner. The bundled fiber guide can comprise a tapered fiber guide, such as a coherent tapered fused fiber; and the energy-distribution tuner can comprise a reflector, such as a cylindrical reflector, for receiving electromagnetic energy from a fiber optic, such as a quartz fiber. Electromagnetic energy from the energy-distribution tuner is coupled to the bundled fiber guide, and then output from the bundled fiber guide at a relatively uniform power density across a predetermined treatment site.

The combination of the energy-distribution tuner and the bundled fiber guide operate together to generate radiation having a relatively uniform power density across an illumination area. The illumination area may have a substantially planar or non-planar topography.

The various embodiments of the present invention may include or address one or more of the following objectives. One objective is to provide a fiber optic coupled to an energy-distribution tuner, wherein electromagnetic radiation exiting the energy-distribution tuner is not concentrated along the fiber optic axis. The energy-distribution tuner can comprise a cylindrical reflector configured to redirect a portion of the electromagnetic radiation back toward a direction of the fiber optic axis. Another objective is to provide a bundled fiber guide having an emission characteristic whereby a power density of electromagnetic radiation exiting the bundled fiber guide is lower than a power density of electromagnetic energy entering the bundled fiber guide. Another objective is to provide a radiation emitting apparatus, which is formed to illuminate the target area with a specific illumination-area shape and/or distribution required for a particular medical or other application. The shape can be non-circular and the distribution can be uniform as measured on a non-planar surface, which can comprise, for example, an arched surface. Yet another objective is to provide an apparatus for providing uniform distributions of power density across an illumination area, with optical losses less than 10%, with a minimal number of optical components, with a simple construct that is relatively easy to make and clean, with reproducible output results, with a construct amenable to miniaturization, and/or with relatively reliable coupling and alignment characteristics. Another objective is to provide an apparatus with a relatively short length, measured in a direction normal to the target.

Any feature or combination of features described herein are included within the scope of the present invention provided that the features included in any such combination are not mutually inconsistent as will be apparent from the context, this specification, and the knowledge of one of ordinary skill in the art. For purposes of summarizing the present invention, certain aspects, advantages and novel features of the present invention have been described herein. Of course, it is to be understood that not necessarily all such aspects, advantages or features will be embodied in any particular embodiment of the present invention. Additional advantages and aspects of the present invention are apparent in the following detailed description and claims.

DETAILED DESCRIPTION OF THE ILLUSTRATED EMBODIMENTS

Figure 1:
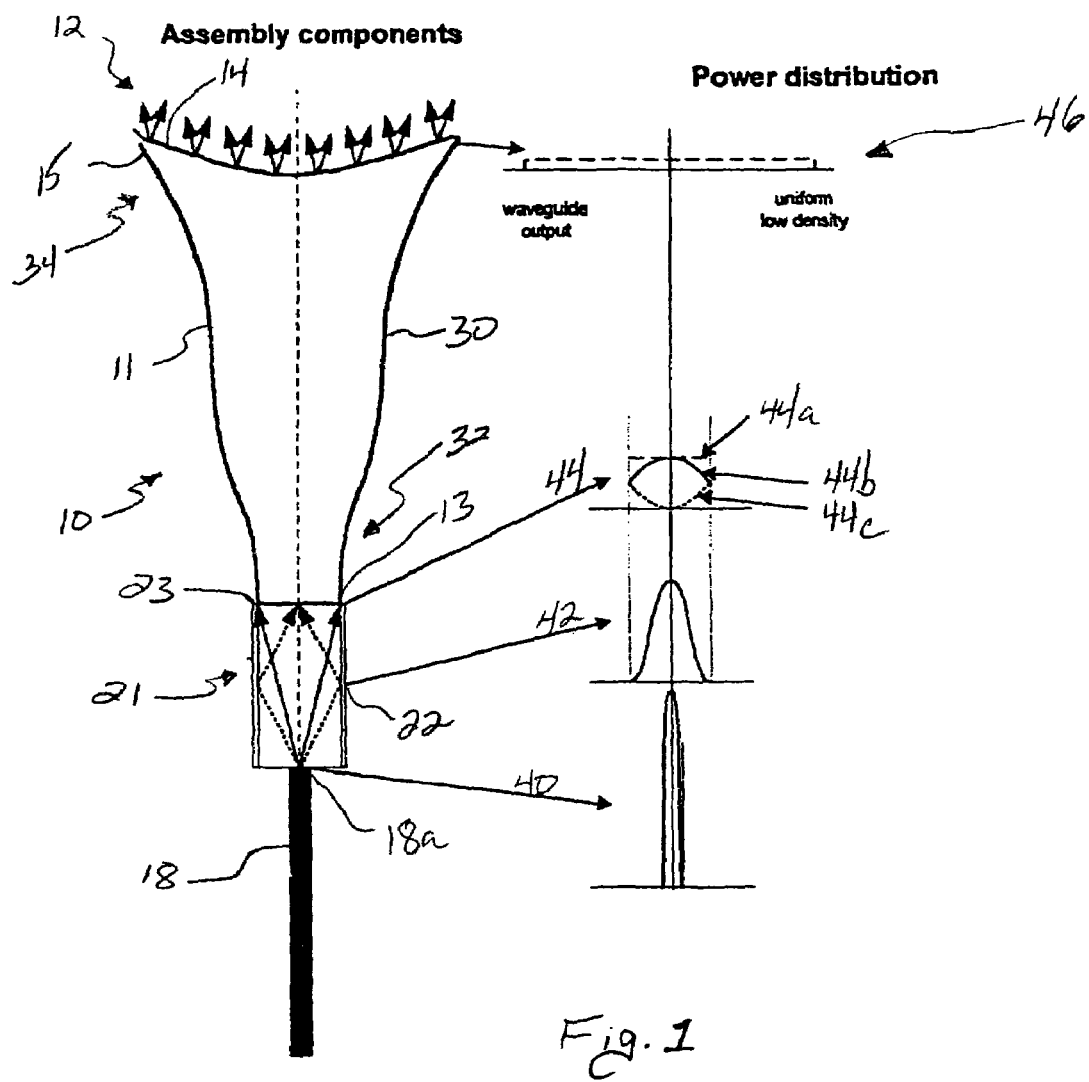
FIG. 1 shows a radiation emitting apparatus designed for uniform illumination of an arched rectangular surface according to the present invention.

Reference will now be made in detail to certain embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

Referring more particularly to the drawings, FIG. 1 shows an exemplary embodiment of a radiation emitting apparatus 10 comprising a bundled fiber guide 11 coupled to an energy distributor that inputs an electromagnetic signal with a cross-sectional power distribution and outputs a signal with a different cross-sectional power distribution than was input. In the illustrated embodiment, the energy distributor comprises an energy-distribution tuner 21. In one embodiment, the bundled fiber guide 11 comprises a coherent fused fiber guide that receives a given spatial distribution of energy at an input end 13 and emits or outputs a similar or the same relative spatial distribution of energy at a different magnification or power density at an output end 15.

In one embodiment, the bundled fiber guide 11 can comprise multiple quartz or glass fiber optics fused together. For example, the bundled fiber guide 11 may comprise 1000 quartz or glass fiber optics fused together, or, in another embodiment, may comprise, for example, ten times that number of fused fiber optics. In an embodiment wherein the bundled fiber guide 11 comprises a coherent tapered fused fiber guide, when a uniform spatial distribution of energy having a relatively high power density is input into the bundled fiber guide 11, a uniform spatial distribution of energy having a lower power density is output from the bundled fiber guide 11. Similarly, in the embodiment wherein the bundled fiber guide 11 comprises a coherent tapered fused fiber guide, when a given spatial distribution of wavelengths is input into the bundled fiber guide 11, the same or about the same spatial distribution of wavelengths having a greater magnification (or lower power density) is output from the bundled fiber guide 11.

The fiber guide 11 is shaped or configured to provide a substantially homogenous beam of electromagnetic radiation from an irregular output end, such as an irregularly shaped output end. In certain embodiments, the fiber guide 11 is configured to emit energy from a non-circular output end having a non-flat or non-planar surface. The apparatus disclosed herein may thus be easier to manufacture relative to existing apparatus, easier to clean, and/or may result in fewer alignment problems. The apparatus may also reduce the number of tolerance issues to provide more reproducible results relative to existing devices.

As shown in FIG. 1, the fiber guide 11 has a tapered configuration. In other words, the fiber guide 11 includes an elongate body 30 having a proximal region 32 and a distal region 34. The distal region 34 has a cross-sectional area that is different than the cross-sectional area of the proximal region 32. In the illustrated embodiment, the cross-sectional area of the distal region 34 is greater than the cross-sectional area of the proximal region 32. A non-planar surface, such as surface 14, is provided at the distal end of the elongate body 30.

The elongate body 30 may taper in a regular or a non-regular pattern. In the illustrated embodiment, the elongate body includes a first portion with a first cross-sectional area, such as the proximal region 32, a second portion having a second cross-sectional area that is different than the first cross-sectional area, such as distal region 34, and a third portion located between the first portion and the second portion, the third portion having a cross-sectional area having dimensions between the cross-sectional areas of the first and second portions. One or more of the portions of the elongate body 30 may include a length where the cross-sectional area remains substantially constant, or in other words, a portion of the elongate body may not be tapered. The transitions from the different portions of the illustrated waveguide 11 are curved, which may be helpful to promote effective light reflectance in the waveguide 11. The elongate body 30 is generally formed of a material that does not permit appreciable amounts of radiation to be emitted from surfaces other than the surface 14. The elongate body 30 may also include a reflective material on an inner surface of the body to affect or facilitate the radiation passing through the elongate body.

Figure 2:
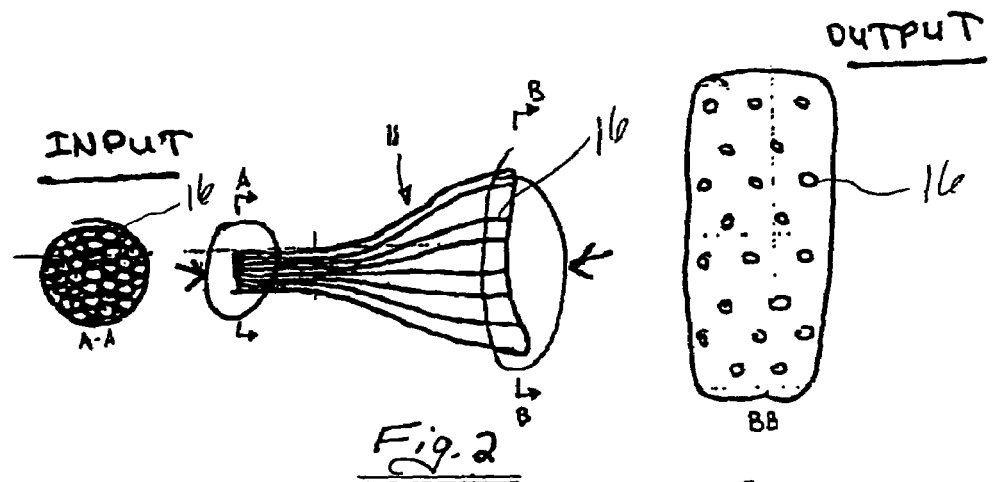
FIG. 2 shows a radiation emitting apparatus in accordance with a first alternative embodiment of the present invention.
Figure 3:
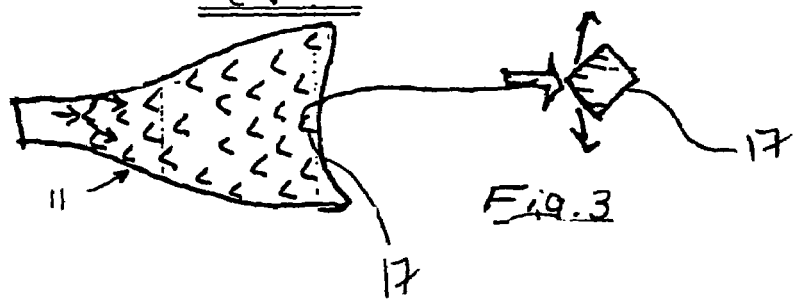
FIG. 3 shows a radiation emitting apparatus in accordance with a second alternative embodiment of the present invention.
Figure 4:
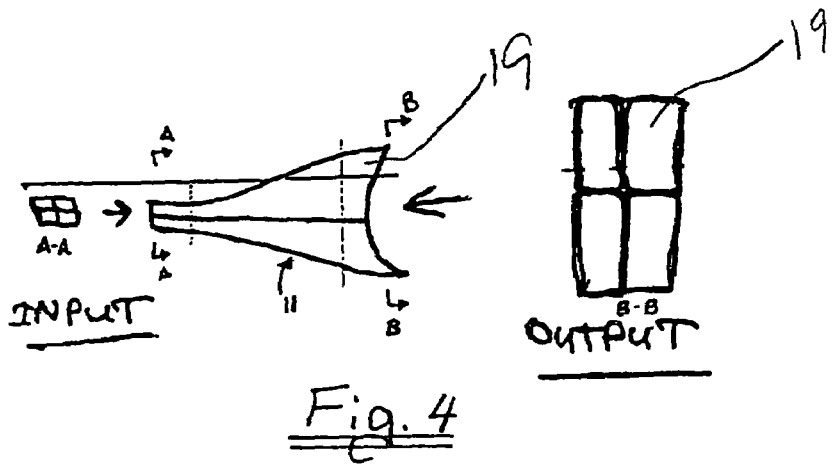
FIG. 4 shows a radiation emitting apparatus in accordance with a third alternative embodiment of the present invention.

FIGS. 2, 3 and 4 show alternative embodiments of the bundled fiber guide 11 of the radiation emitting apparatus 10. With reference to FIG. 2, the fibers 16 of the fiber guide 11 have about the same diameters throughout and along their lengths, and are uniformly distributed, or in another embodiment approximately uniformly distributed or in another embodiment somewhat uniformly distributed, in a filling material. In other embodiments, at least the distal ends but not necessarily the other portions of the fibers 16, are uniformly distributed or approximately uniformly distributed or somewhat uniformly distributed, in the filling material. The filling material can comprise an opaque or semi-opaque plastic, and/or can comprise, for example, an opaque or semi-opaque silicon or epoxy. In one embodiment, the fibers (e.g., the distal ends of the fibers) can be held in a uniformly distributed fashion, for example, with a tool during filling and hardening of the filling material; and, after the filler hardens, the ends may be cut and/or polished.

With reference to FIG. 3, the filler of the fiber guide or waveguide 11 is preferably optically transparent, comprising, for example, clear epoxy or glass. In certain ones of such embodiments, the fiber guide 11 may include multiple beam-splitting mirror elements 17. The single mirror elements 17 may comprise spherical structures, flat structures (such as glitter-type elements found in metallic paint), cubical or rectangular structures, crystalline structures (made of diamond, sapphire, or other materials), rods, prisms, or other shapes. In the illustrated embodiment, wherein the single mirror elements 17 comprise cubes coated with or formed of a reflective material, such as silver, aluminum or gold, light passing through the filler is reflected by the single mirror elements. The reflected light then interacts with other single mirror elements 17 in the filler, and also reflects (e.g., in a distal direction) off of a reflective coating on the boundary of the tapered filler. The reflective coating may comprise a silver, aluminum or gold coating, depending on wavelength as with the other reflective materials set forth herein. Regarding the single mirror elements, their diameters in one embodiment are within a range of from several times the wavelength of the electromagnetic energy to about 0.5 or 1 mm. Other sizes may be implemented in modified embodiments. In some embodiments, the single mirror elements are not formed of or coated with a reflective material; for example, in one preferred embodiment, the single mirror elements comprise balls, formed of sapphire. The single mirror elements can be uniformly distributed, or in another embodiment approximately uniformly distributed or in another embodiment somewhat uniformly distributed, in the filling material using known methods of suspending particles in for example a viscous medium such as electromagnetic waves and/or shaking/spinning. In embodiments like that shown in FIG. 3, fiber optic fibers may not be located in the fiber guide 11 since or to the extent the desired light emitting properties may be obtained by the mirror elements 17.

In the embodiment of FIG. 4, the bundled fiber guide 11 comprises a plurality of hollow waveguides 19. The waveguides 19 may comprise similar materials as those used to form the fibers 16 described herein, or may comprise other materials. The waveguides 19 can comprise glass, plastic, metal, or other waveguide materials. In some embodiments, the waveguides 19 can comprise hollow sapphire or nickel. In the illustrated embodiment, the waveguides 19 have cross-sectional areas and/or diameters that increase in the distal direction. The cross-sectional shapes may be rectangular or oval, for example. As presently embodied, the waveguides 19 can be formed by heating followed by deformation to attenuate the cross-sectional areas and/or diameters at the proximal ends of the waveguides 19, while generating a tapered effect along the lengths of the waveguides 19. For example, the waveguides 19 may be heated and then pulled and/or compressed with a greater percentage of the pulling and/or compressing occurring near the proximal ends of the waveguides. After the waveguides 19 have been shaped, their interior surfaces may be coated with reflective or semi-reflective materials, such as silver and germanium, aluminum, aluminum oxide, silver or gold. In the embodiment shown in FIG. 4, the bundled fiber guide 11 may or may not include additional fiber optic fibers depending on the need of the user of the apparatus.

The radiation emitting apparatus 10 can be housed in a handpiece, which can comprise an ergonomic design. An optional protective cap cover may be attached to the handpiece or the radiation emitting apparatus 10. The cap, which is preferably substantially transparent to the output radiation, can be disposable and can comprise, for example, a snap-on construction to facilitate rapid attachment and removal thereof. The cap can further ensure clean surfaces of the applied parts. This cap, or in another embodiment the handpiece itself, may have spacers or feet that provide a predetermined distance or spacing between the apparatus and the target (e.g., teeth) surfaces to distribute the energy in a predetermined manner (e.g., at a certain concentration and/or uniformity). In one embodiment, the arched surface 14 can be spaced about 1 mm from the teeth by the spacers.

A fiber optic cable 18 is coupled to the radiation emitting apparatus 10 via the energy-distribution tuner 21. The fiber optic 18 can be made of materials, such as sapphire, or other materials disclosed in U.S. Pat. No. 5,741,247, the entire contents of which are incorporated by reference herein to the extent compatible and/or not mutually exclusive with the apparatus and methods of the present invention. The energy-distribution tuner 21 according to the invention couples the fiber optic 18 to the bundled fiber guide 11. The energy-distribution tuner 21 converts an energy distribution at its input into a different energy distribution at its output. In accordance with one aspect of the present invention, the energy-distribution tuner 21 comprises a reflector, and in a particular embodiment the energy-distribution tuner comprises a cylindrical reflector. A longitudinal center axis of the energy-distribution tuner 21, configured as a cylindrical reflector, can be aligned with a longitudinal center axis of the fiber optic 18, as shown in FIG. 1. The energy-distribution tuner 21, configured as a cylindrical reflector, can comprise, for example, an outer diameter of about 5 mm and a mirrored inner surface.

Although in the illustrated embodiment, the energy-distribution tuner 21 comprises a reflective cylinder and the output end of the fiber optic 18 is planar, other shapes of both devices can be incorporated in modified embodiments to achieve various spatial energy distributions at the output of the energy-distribution tuner 21. For example, the fiber optic output end may have spherical, conical, chiseled or other light-intensity altering (e.g., dispersing) shapes in modified embodiments.

In one embodiment the coupling of the fiber optic 18 cable to the energy-distribution tuner 21 occurs within the handpiece of the radiation emitting apparatus 10, wherein the fiber optic 18 cable can comprise either metal or a built-in metal tubing to attenuate any possible fiber optic damage. The fiber optic itself 18 can comprise, for example, a 600 um diameter quartz fiber, and can be disposed within the fiber optic cable whereby the fiber optic cable is fixed both at an electromagnetic energy source side (not shown) and at the radiation emitting apparatus 10.

The energy-distribution tuner 21 can be constructed to emit electromagnetic radiation in a nonconcentrically-focused manner, relative to its input which can be a cylindrically-shaped fiber optic end (i.e., a truncated fiber end). Output radiation from the energy-distribution tuner 21 (and, also, from the radiation emitting apparatus 10) can be engineered to have a spatial energy distribution which differs from the spatial energy distribution of a conventional truncated fiber end. More particularly, in accordance with an aspect of the present invention, the energy-distribution tuner 21 (and, also, the radiation emitting apparatus 10) is constructed to generate output radiation having a spatial energy distribution with one or more energy concentrations or peaks located in areas other than a center of the spatial energy distribution. The center of the spatial energy distribution can be defined as an area aligned with (or intersecting) an optical fiber axis of the apparatus or an area aligned with (or intersecting) an average direction of propagation of the output radiation. According to one aspect, the center of the spatial energy distribution can be defined as a central part of a cross-section of the output radiation taken in a direction orthogonal to the direction of propagation of the output radiation.

With reference to FIG. 1 in particular, the energy-distribution tuner 21 may be constructed to convert a "Gaussian" distribution of the laser radiation that is emitted from fiber optic 18 into a different distribution. At the output end 18a of the fiber optic 18, light is typically emitted as a uniform circular spot having a maximal power along the center of an optical or longitudinal axis of the fiber optic 18. An example of a power distribution for the output end 18a is shown at 40.

Toward the middle region 22 of the energy distribution tuner 21, the power distribution has a substantially "Gaussian" shape (as shown at 42) with the width of the light beam being greater than at the output end 18a of fiber optic 18. The energy-distribution tuner 21 is configured to superimpose or mix direct beams with a hotter center (e.g., greater power) with reflected beams, which form a warm peripheral region (e.g. less power than the center). The energy-distribution tuner 21 is thus able to relatively uniformly distribute the light beams over a geometric shape, such as a circular shape, at a certain plane (e.g., output surface 23).

The input end 13 of the fiber guide 11 is coupled to the energy-distribution tuner 21 at that plane (e.g., output surface 23). Thus, in the exemplary illustrated embodiment of FIG. 1, the plane is denoted by output surface 23. The power distribution at the output surface 23 is shown at 44. In the graph 44 of the power distribution at the output surface 23 of the energy-distribution tuner, the average-uniform, high density radiation is shown at 44a, the direct laser beams are shown at 44b, and the reflected laser beams are shown at 44c. Thus, the uniform distribution with a high power density is projected from the output surface 23 to a uniform distribution at a low power density at surface 14, and as shown by the power distribution 46.

The output radiation in one embodiment has a spatial energy distribution which is relatively uniform across a geometric surface intersecting the output radiation. The geometric surface can be for example orthogonally disposed relative to the output radiation. In the illustrated embodiment, the geometric surface is curved in the context of describing output radiation 12 from the radiation emitting apparatus 10 but is planar in the context of describing output radiation from the energy-distribution tuner 21. In other embodiments the geometric surface can be planar in the context of describing output radiation from the radiation emitting apparatus 10. A curved geometric surface can approximate a curved surface of the treatment site, so that when the treatment site is aligned with the curved geometric surface the treatment site is irradiated uniformly with about the same energy at all of the points on the treatment site. The treatment site can comprise, for example, a part of the body, such as a row of teeth, an elbow, a wrist, or a portion of the jaw to be treated for temporomandibular joint (TMJ) disorders or conditions, wherein the curved geometrical surface is designed to follow the envelope of the anatomical area requiring treatment.

In the illustrated embodiment, and as shown in FIG. 1, a uniform power distribution is generated over the area of a curved geometrical surface, such as the arched surface 14, which has a rectangular boundary of for example about 33 mm by about 7 mm. In this embodiment, the output radiation is applied uniformly within the rectangular boundary. The treatment site in the illustrated embodiment comprises the upper arch of teeth in the mouth, whereby the curved geometric surface defining the light emitting area of the apparatus is shaped as an arched rectangular surface 14 to follow the anatomy of the upper arch of teeth. A variation on the design of the radiation emitting apparatus 10 may be so configured that it can direct electromagnetic energy on the front, back or occlusal surfaces of the target surface (e.g., teeth). The radiation emitting apparatus 10 may also be used, for example, for whitening teeth, bio-stimulation, caries prevention, caries detection (in combination with filtered eyeglasses to visualize and detect emitted fluorescent light), desensitizing teeth, and composite curing (restorations, laminates, brackets for braces).

Electromagnetic energy can be supplied at wavelengths from about 0.4 μm to about 11 μm, and in certain embodiments from about 0.4 μm to about 3 μm, from a light source such as a plasma arc lamp, a LED, or a laser having a continuous wave (CW) or pulsed mode of operation. In an exemplary embodiment, the electromagnetic energy is laser radiation from a semiconductor diode laser source, delivering up to 10 W CW at an 815+/−10 nm wavelength. In one exemplary embodiment, for a rectangular area of 33 mm by 7 mm, the output energy density can be about 3 to 4 W/cm$^2$. In another embodiment, the electromagnetic energy is non-coherent light from a zenon arc lamp with an output energy density of about 1 W/cm$^2$ across a rectangular area of 33 mm by 7 mm, and this output can be applied continuously to a target, such as teeth, for 10 to 40 seconds. The output area may be larger or smaller, and in one embodiment the output area of the bundled fiber guide 11 may have a maximum dimension of, for example, about 8 to 12 mm.

As presently embodied, the radiation emitting apparatus 10 can comprise a relatively short length, measured in a direction normal to the target. More particularly, as presently embodied the length, measured in a direction normal to the target, can be about 35 mm between the distal end of the bundled fiber guide 11 and the proximal end of the energy-distribution tuner 21. In accordance with an aspect of the present invention, the energy-distribution tuner 21 is formed so as, when combined with the bundled waveguide 11, to provide a desirable distribution of power (e.g., a relatively uniform power density) across the topography of a predetermined treatment site (e.g., a surface topography corresponding to the arched surface 14). In other embodiments, energy-distribution tuners 21 can be combined with bundled fiber guides 11 to generate distributions of energy on a curved geometrical surface in the form of, for example, one or more of an outline or ring shape, a gradual transition, or a uniform distribution.

The diameter and construction of the fiber optic 18, and the position and orientation of the fiber optic 18 adjacent to or inside the energy-distribution tuner 21, may be interdependent and in the illustrated example can be selected to provide a desired (e.g., very uniform) distribution of radiation power over the output surface 23 of the energy-distribution tuner 21. By uniform distribution, it is meant that an energy density (or power density) on a predetermined area (e.g., 3 mm$^2$) of the geometrical surface (e.g., output surface 23 or arched surface 14) is within plus or minus about 5% of the average energy or power density of the geometrical surface (i.e., illuminated area). In another embodiment, the power density of a predetermined area of the geometrical surface can be within plus or minus about 50% of the total average power density of the geometrical surface. In a modified embodiment, uniform distribution can mean that an energy density (or power density) on a predetermined area of the geometrical surface is within plus or minus about 5% of that of an adjacent area of the same size. In contrast, the variance between a power density of a central area of a prior-art truncated fiber end can be 200 to 1000% greater than the average power density of the total illuminated area.

The radiation emitting apparatus 10 may be used with a gel for whitening teeth, caries prevention, caries detection, and desensitizing teeth. The gel can comprise one or more of the following: (a) A target chromophore that could be a pigment, dye or chemical compound (Ultramarine Violet, Ultramarine Blue, '4301 Black', Caramel, or Black oxide), strongly absorbed by laser wavelengths in the infrared from 700 nm to 3 microns. (b) Furthermore, organic and inorganic pigments and dyes, and other food, drug and cosmetic color additives, which include, but are not limited to, the following: Complex inorganic odor pigments for shades of black, brown, red, yellow, green, blue and violet; Beta Carotene (orange/yellow); Riboflavin (orange/yellow); Iron oxides (black, brown, yellow and red); Ultramarines (green, blue, violet and red); Chromium oxide green; grape skin extract; dehydrated beets; and annalto extract (orange), can be implemented for activation by visible or infrared wavelengths. (c) Another type of additives are Epolight dyes for laser protective eyewear, which are disclosed in U.S. Provisional Application No. 60/314,858 and incorporated herein by reference to the extent compatible and/or not mutually exclusive with the apparatus and methods of the present invention, and which can be implemented with the gel because of their specific selective absorption at the specific laser wavelength. (d) Agents to increase activation of the whitening substance such as metal powders (i.e. copper, bronze powder). (e) A whitening substance (including, but not limited to hydrogen peroxide or Carbamide peroxide) is capable of breaking down and removing stains in target material when activated by laser/EM energy directly, or via target chromophore absorption. (f) Substances for preventing or prohibiting caries development, such as Calcium fluoride, Amine fluoride, Sodium fluoride, Sodium monofluorophosphate, and Stannous fluoride are also considered as additives to the gel. The fluoride compound may also be used together with antibacterial agents capable of killing *Streptococcus sangius, Streptococcus mutans, Actinomyces viscosus*, and other bacteria associated with tooth caries. These agents may include benzol-konium chloride, phenol, stannous fluoride, sodium phenolate, sodium lauryl sulfate, sodium N-lauroyl sarcosinate, or sodium cocomonoglyceride sulfonate. (g) Another substance, Potassium nitrate, can be added to the gel for desensitizing effects on teeth.

The whitening substance could be hydrogen peroxide, carbamide peroxide or some other whitening substance, which could comprise up to 50% of the whitening gel. The pigment concentration can comprise up to 50% of the gel composition. In more specific embodiments, it comprises between 0.01% and 15% of the gel composition.

The following steps describe the method of using the whitening gel with the handpiece to whiten human teeth: (a) apply a layer of gel over the teeth surfaces; (b) place the handpiece above the gel-covered surfaces, on the upper or lower arch of the mouth; (c) activate the laser for the prescribed time duration; (d) wait for a predetermined period of time and activate the laser again if necessary.

In one embodiment, the laser is activated for 1-10 seconds. In another embodiment, the laser is activated for 10-30 seconds. In another embodiment, the laser is activated for 30-60 seconds. Laser activation times of over one minute could be applied depending on the type of stain and power density setting. The waiting period between exposures may be from 0 seconds to 15 minutes in one embodiment, or between 15 and 30 minutes in another embodiment. The laser power density may be, although not limited to, in the range of 0 W/cm$^2$-50 W/cm$^2$. In one embodiment, the power density is around 3 W/cm$^2$. An example of a full-mouth procedure can be performed by following these steps:

1) Divide the upper and lower arches of teeth into four quadrants, with each quadrant having up to 4 teeth or more.

2) Apply whitening gel to the teeth to be treated.

2.1) Direct the whitening handpiece toward the first quadrant, using a laser power density of 3 W/cm$^2$.

2.2) Activate the laser for 15 seconds, and then stop.

2.3) Repeat the same procedure for the second, third and fourth quadrants.

2.4) Wait for a period of 1 minute and repeat steps 2.1-2.4 a further three to ten times depending on the condition of the patient's teeth.

2.5) Remove the whitening gel from the teeth.

3) Repeat the treatment steps up to two more times depending on the nature of the patient's stain.

The above is just one example of a tooth whitening method using the whitening gel and handpiece. The time of exposure and number of applications can vary depending on the patient, and thus the invention is not limited to the example procedure described above.

Laser energy in medicine is usually used as a surgical tool to remove tissue. Low Level Laser Therapy (LLLT) uses laser energy at power levels below those required to cut or ablate tissue, to nonthermally and nondestructively alter cellular function.

Nerve tissue, according to the literature, has a photosensitive component which reacts to laser exposure, reducing the excitability of the nerve cells by interrupting the fast pain fibers with a resultant reduction in pain. LLLT has also been shown to accelerate the repair process of crush-damaged nerves and improve function in both the CNS and peripheral nerves after injury.

The proposed delivery handpiece can be used to treat a number of symptoms and conditions, including: (a) pain reduction when directed at acupuncture points and muscular trigger points and when used to treat chronic tendinopathies, degenerative arthritis, rheumatoid arthritis, muscle pain, tendonitis. tension myalgia, chronic radiculopathy, chronic neuropathy, acute soft tissue pain; also a reduction in tissue swelling, bruising and TMJ disorders or conditions. (b) treatment of myofacial and postoperative pain; muscle tears; hematomas; tendonitis; shingles; herpes simplex; scarring; burn and wound healing According to this invention, the handpiece is designed in a shape and size broadly corresponding to the area to be treated, and will evenly distribute the energy over the target area. The electromagnetic wavelength for this device can be between 0.4-11 nm. Typical power output levels for a treatment can range from 10-700 mW, more specifically 15-100 mW. Energy levels can range from 0-8 J/cm$^2$, more specifically 0-4 J/cm$^2$. Treatment time can be between 10 seconds to 10 minutes, and more specifically 10 seconds to 4 minutes. Repeated treatments may be required on the same day and at different time intervals, or at different dates.

In a procedure utilizing this device, the clinician will point the handpiece toward either the tissue site requiring treatment, acupuncture points, or muscle trigger points, and then direct laser energy toward the target for a given period of time.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

What is claimed is:

1. A radiation emitting apparatus, comprising:
a fiber optic end;
an energy-distribution tuner adapted to receive radiation from the fiber optic end and constructed to generate a distribution of radiation at an output of the energy-distribution tuner, at least part of the distribution of radiation being generated at the output with a first magnification; and a fiber guide or waveguide comprising a coherent tapered fused fiber and constructed to direct energy from the energy-distribution tuner in a direction away from the fiber guide or waveguide with a second magnification greater than the first magnification.

2. The radiation emitting apparatus as set forth in claim 1, wherein the energy-distribution tuner comprises a cylindrical reflector.

3. The radiation emitting apparatus as set forth in claim 1, wherein:
the energy-distribution tuner comprises a cylindrical reflector; and
the fiber optic end is centered to emit energy through the cylindrical retlector.

4. The radiation emitting apparatus as set forth in claim 3, wherein a longitudinal center axis of the cylindrical reflector is aligned with a longitudinal center axis of the fiber optic end.

5. The radiation emitting apparatus as set forth in claim 4, wherein the radiation emitting apparatus is disposed within a handpiece.

6. The radiation emitting apparatus as set forth in claim 1, wherein the fiber guide or waveguide is coupled to the energy-distribution tuner to receive a uniform distribution of high power energy therefrom, and is configured to emit a substantially uniform distribution of energy having a lower power than received from the energy distribution tuner.

7. A radiation emitting apparatus, comprising:
a fiber optic end able to emit radiation;
an energy-distribution tuner constructed to receive radiation from the fiber optic end and generate a distribution of radiation at an output of the energy-distribution tuner, at least part of the distribution of radiation being generated at the output with a first magnification; and
a fiber guide or waveguide configured to emit a substantially uniform distribution of energy from an irregularly shaped output end and constructed to direct energy from the energy-distribution tuner in a direction away from the fiber guide or waveguide with a second magnification greater than the first magnification.

8. The radiation emitting apparatus as set forth in claim 7, wherein the irregularly shaped output end includes a curved surface having a non-circular cross-section.

9. A radiation emitting apparatus, comprising:
a fiber optic end adapted to emit radiation;
an energy-distribution tuner constructed to generate a distribution of the radiation from the fiber optic end at an output of the energy-distribution tuner, at least part of the distribution of radiation being generated at the output with a first magnification; and
a fiber guide or waveguide including a plurality of fused optic fibers and constructed to direct energy from the energy-distribution tuner in a direction away from the fiber guide or waveguide with a second magnification greater than the first magnification.

10. A radiation emitting apparatus, comprising:
a fiber optic end;
an energy-distribution tuner coupled to the fiber optic end: and
a fiber guide or waveguide constructed to direct energy emitted from the energy-distrubition tuner along a path and in a direction away from the fiber guide or waveguide and including a plurality of elements, at least some of which have positions in close proximity to the path and diameters less than about 1 mm, and tapered waveguides.

11. A radiation emitting apparatus, comprising:
a fiber optic end;
an energy-distribution tuner coupled to the fiber optic end and constructed to generate a distribution of radiation at an output of the energy-distribution tuner, at least part of the distribution of radiation being generated at the output with a first magnification; and
a fiber guide or waveguide constructed to direct energy from the energy-distribution tuner in a direction away from the fiber guide or waveguide with a second magnification greater than the first magnification and including an elongate body with a first end having a first cross-sectional area and a second end having a second cross-sectional area that is different than the first cross-sectional area, the second end including a curved surface for emitting energy received from the energy distribution tuner toward a target surface.

12. A method comprising:
providing a radiation emitting apparatus with a fiber optic end, an energy-distribution tuner generating a distribution of radiation at an output of the energy-distribution tuner with at least part of the distribution being generated at the output with a first magnification, and a fiber guide or waveguide constructed to direct energy from the energy-distribution tuner in a direction away from the fiber guide or waveguide with a second magnification greater than the first magnification;
reflecting radiation in an energy distributor to generate a distribution of the radiation at an output of the energy distributor, the distributed radiation having a first power; and
directing the distributed radiation through a fiber guide or waveguide to form a distribution of radiation having a second power that is substantially different from the first power whereby the distribution of radiation having the second power is directed away from the fiber guide or waveguide.

13. The method as set forth in claim 12, wherein:
the reflecting is preceded by directing radiation from a fiber optic end toward the energy distribution tuner; and
the radiation is directed toward a dental surface of a patient.

* * * * *